United States Patent [19]
Hoffmann et al.

[11] 3,952,098
[45] Apr. 20, 1976

[54] COMPOSITIONS AND METHODS OF COMBATTING INSECTS AND ACARIDS USING PYRAZOLO-(THIONO)-PHOSPHORIC(-PHOSPHONIC) ACID ESTERS

[75] Inventors: Hellmut Hoffmann, Wuppertal-Elberfeld; Ingeborg Hammann, Cologne; Gunter Unterstenhofer, Opladen, all of Germany

[73] Assignee: Bayer Aktiengesellschaft, Leverkusen, Germany

[22] Filed: June 29, 1973

[21] Appl. No.: 375,209

Related U.S. Application Data

[62] Division of Ser. No. 165,390, July 22, 1971, Pat. No. 3,839,355.

[30] Foreign Application Priority Data

July 30, 1970  Germany............................ 2037853

[52] U.S. Cl. .................................................. 424/200
[51] Int. Cl. ........................ A01n 9/22; A01n 9/36
[58] Field of Search .................................... 424/200

[56]  References Cited
UNITED STATES PATENTS

| | | |
|---|---|---|
| 2,754,244 | 7/1956 | Gysin et al. ..................... 260/310 R |
| 2,998,426 | 8/1961 | Dickinson et al. ............... 260/310 R |
| 3,111,525 | 11/1963 | Meltzer et al. ................... 260/310 R |
| 3,216,894 | 11/1965 | Lorenz et al. .................... 260/310 R |
| 3,728,297 | 4/1973 | Hoffmann et al. .............. 260/310 R |

*Primary Examiner*—Jerome D. Goldberg
*Assistant Examiner*—Allen J. Robinson
*Attorney, Agent, or Firm*—Burgess, Dinklage & Sprung

[57]  ABSTRACT

Pyrazolo-(thiono)-phosphoric(phosphonic) acid esters of the general formula

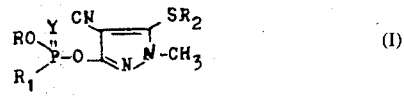

in which
R is alkyl with 1–6 carbon atoms,
$R_1$ is alkyl or alkoxy with 1–6 carbon atoms,
$R_2$ is alkyl with 2–4 carbon atoms, and
Y is oxygen or sulfur, which possess insecticidal, acaricidal, rodenticidal, fungicidal and nematocidal properties.

11 Claims, No Drawings

COMPOSITIONS AND METHODS OF COMBATTING INSECTS AND ACARIDS USING PYRAZOLO-(THIONO)-PHOSPHORIC(PHOSPHONIC) ACID ESTERS

This is a division of application Ser. No. 165,390, filed July 22, 1971, now U.S. Pat. No. 3,839,355. The present invention relates to and has for its objects the provision of particular new pyrazolo-(thiono)-phosphoric(phosphonic) acid esters, i.e. 0,0-dialkyl-0-[1-methyl-4-cyano-5-ethyl-(or propyl- or butyl-)mercaptopyrazol(3)yl] (thiono)phosphoric acid esters and the corresponding alkanephosphonic acid esters, which possess insecticidal, acaricidal, rodenticidal, fungicidal and nematocidal properties, active compositions in the form of mixtures of such compounds with solid and liquid dispersible carrier vehicles, and methods for producing such compounds and for using such compounds in a new way especially for combating pests, e.g. insects, acarids, rodents, fungi and nematodes, especially insects and acarids, with other and further objects becoming apparent from a study of the within specification and accompanying examples.

From U.S. Pat. No. 2,754,244 it is known that methylpyrazolo-(thiono)-phosphoric acid esters, such as 0,0-dimethyl- (Compound A) or 0,0-diethyl-0-[5-methylpyrazol (3)yl]-thionophosphoric acid ester (Compound B), possesss an insecticidal and acaricidal activity.

The present invention provides pyrazolo-(thiono)-phosphoric(phosphonic) acid esters of the formula

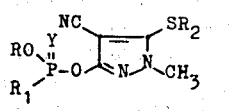
(I)

in which
R is alkyl with 1–6 carbon atoms,
R₁ is alkyl or alkoxy with 1–6 carbon atoms,
R₂ is alkyl with 2–4 carbon atoms, and
Y is oxygen or sulfur.

It has surprisingly been found that these compounds exhibit strong insecticidal and acaricidal properties and often strong rodenticidal, fungicidal and nematocial properties, as well.

The invention also provides a process for the production of a pyrazolo-(thiono)-phosphoric(phosphonic)acid ester of the formula (I) in which a (thiono)phosphoric(phosphonic) acid ester halide of the formula

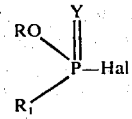
(II)

is reacted with a 1-methyl-3-hydroxy-4-cyano-5-alkyl-mercaptopyrazole of the formula

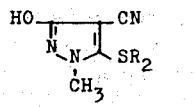
(III)

in the form of a salt or in the presence of an acid-binding agent,

R, R₁, R₂ and Y in the aforesaid formulae possessing the meanings stated above, while
Hal stands for halogen, preferably chlorine.

Surprisingly, the pyrazolo-(thiono)-phosphoric(phosphonic) acid esters according to the invention are distinguished by a considerably better insecticidal, in particular soil-insecticidal, and acaricidal, activity than the known methylpyrazolo-(thiono)-phosphoric acid esters of analogous constitution and the same direction of activity. The compounds according to the invention therefore represent a genuine enrichment of the art.

If, for example, 0,0-diethylthionophosphoric acid diester chloride and 1-methyl-3-hydroxy-4-cyano-5-ethylmercaptopyrazole are used at starting materials, the reaction course can be represented by the following formula scheme:

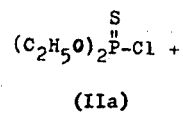
(IIa)

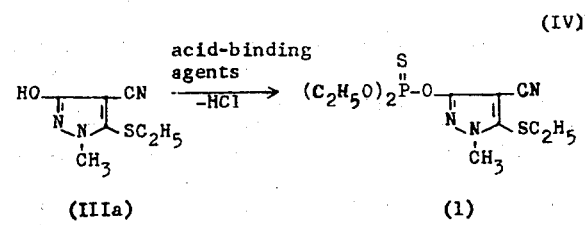
(IIIa)    (1)

In the foregoing formulae, R and R₁ preferably are straight-chain or branched lower alkyl radicals with 1 to 4 carbon atoms, such as methyl, ethyl, n- or iso-propyl, or n-, iso-, sec.- or tert.-butyl. Alternatively, R₁ may also preferably be a lower alkoxy group with 1 to 4 carbon atoms. R₂ is preferably ethyl, propyl or isopropyl.

As examples of the (thiono)-phosphoric(phosphonic) acid ester halides (II) to be used according to the process there are mentioned in particular:

0,0-dimethyl-, 0,0-diethyl-, 0,0-dipropyl-, 0,0-di-iso-propyl-, 0-methyl-0-ethyl-, 0-methyl-0-iso-propyl-, 0-ethyl-0-iso-propyl-phosphoric acid ester chloride or the appropriate thiono analogues; further, 0-methyl-methane-, 0-ethyl-propane, 0-iso-propyl-ethane-, 0-butyl-methane-phosphonic acid ester chloride and the appropriate thiono compounds.

The (thiono)phosphoric(phosphonic) acid ester halides of the constitution (II) required as starting materials are known from the literature and, like the pyrazone derivative of the constitution (III) whose synthesis is described in Example 7 hereinbelow, are readily accessible, even on an industrial scale.

The preparative process is preferably carried out with the use of suitable solvents or diluents. As such, practically all inert organic solvents are suitable. These include, in particular, aliphatic and aromatic optionally chlorinated hydrocarbons, such as benzene, toluene, xylene, benzine, methylene chloride, chloroform, carbontetrachloride, chlorobenzene; ethers, such as diethyl and dibutyl ether, dioxane; ketones, for example acetone, methyl ethyl, methylisopropyl and methylisobutyl ketone; and nitriles, such as aceto- and propionitrile.

As acid acceptors, all customary acid-binding agents can be used. Particularly good results have been obtained with alkali metal carbonates and alcoholates, such as sodium and potassium carbonate, methylate or ethylate; further, aliphatic, aromatic or heterocyclic amines, for example triethylamine, dimethylamine, dimethylaniline, dimethylbenzylamine and pyridine.

The reaction temperature can be varied within a fairly wide range. In general, the reaction is carried out at about 40° to 120°, preferably at about 75° to 85°C.

The reaction is, in general, carried out at normal pressure.

For carrying out of the process, the starting materials are in most cases used in equimolar proportions. An excess of one or other of the reaction components brings no substantial advantages. The reaction is preferably carried out in the presence of one of the above-mentioned solvents, as well as in the presence of an acid acceptor, at the temperatures stated. After several hours stirring — optionally with heating — the reaction mixture is poured into water, taken up with a hydrocarbon, preferably benzene, and worked up in accordance with customary processes.

The products according to the invention are obtained in most cases in the form of colorless to slightly yellow colored, viscous, water-insoluble oils which cannot be distilled without decomposition but can, by so-called "slight distillation", that is, by longer heating to moderately elevated temperatures, be freed from the last volatile components and in this way be purified. For their characterization the refractive index is especially useful.

As already mentioned above, the new pyrazolo-(thiono)-phosphoric(phosphonic) acid esters are distinguished by an outstanding insecticidal and acaricidal effectiveness against crop pests, hygiene pests and pests of stored products. They possess a good activity against both sucking and eating insects and mites (Acarina). At the same time, they exhibit a low phytotoxicity. Often they exhibit substantial rodenticidal, fungicidal and nematocidal activity. The products according to the invention are therefore useful as pesticides, above all in crop protection and the protection of stored products, as well as in the hygiene field.

To the sucking insects contemplated herein there belong, in the main, aphids (Aphidae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus Korscheltitl*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus;* and the like.

In the case of the biting insects comtemplated herein, above all there should be mentioned butterfly caterpillars (Lepidoptera) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kühniella*) and greater wax moth (*Galleria mellonella*); and the like.

Also to be classed with the biting insects contemplated herein are beetles (Coleoptera), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (Bruchidius = *Acanthoscelides obtectus*), the leather beetle (*Dermestes frischi*), the khapra beetle (*Trogoderma granarium*), the flour beetle (Tribolium castaneum), the northern corn billbug (Calandra or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (Agriotes spec.) and larvae of the cockchafer (*Melolontha melolontha*); cockroaches, such as the German cockroach (*Blattella germanica*), American cockroach (*Periplaneta americana*), Madeira cockroach (Leucophaea or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta;* further, Orthoptera, for example the house cricket (*Acheta domesticus*); termites such as the eastern subterranean termite (*Reticulitermes flavipes*) and Hymenoptera such as ants, for example the garden ant (*Lasius niger*); and the like.

The Diptera contemplated herein comprise essentially the flies, such as the vinegar fly (*Drosphila melanogaster*), the Mediterranean fruit fly (*Ceratitis capita*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (Aedes aegypti), the northern house mosquito (*Culex pipiens*) and the malaria mosquito (*Anopheles stephensi*); and the like.

With the mites (Acari) contemplated herein there are classed, in particular, the spider mites (Tetranychidae) such as the two-spotted spider mite (*Tetranychus telarius* = *Tetranychus althaeae* or *Tetranychus urticae*) and the European red mite (*Paratetranychus pilosus* = *Panonychus ulmi*), gall mites, for example the black currant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*); and the like.

When applied against hygiene pests and pests of stored products, particularly flies and mosquitoes, the novel products are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g., conventional pesticide disperisble carrier vehicles such as gases, solutions, emulsions, suspensions, emulsifiable concentrates, spray powders, pastes, soluble powders, dusting agents, granules, etc. These prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, etc.), halogenated, especially chlorinated, aromatic hydrocarbons (e.g. chlorobenzenes, etc.), paraffins (e.g. petroleum fractions), chlorinated aliphatic hydrocarbons (e.g. methylene chloride, etc.), alcohols (e.g. methanol, ethanol, propanol, butanol, etc.), amines (e.g. ethanolamine, etc.), ethers, ether-alcohols (e.g. glycol monomethyl ether, etc.), amides (e.g. dimethyl formamide, etc.), sulfoxides (e.g. dimethyl sulfoxide, etc.), ketones (e.g. acetone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, keiselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfonates, aryl sulfonates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, acaricides, rodenticides, fungicides and nematocides, or bactercides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent an/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects, acarids, rodents, fungi and nematodes and more particularly methods of combating at least one of insects and acarids, which comprises applying to at least one of correspondingly (a) such insects, (b) such acarids, (c) such rodents, (d) such fungi, (e) such nematodes and (f) the corresponding habitat thereof, i.e. the locus to be protected, a correspondingly combative or toxic amount, i.e. an insecticidally, acaricidally, rodenticidally, fungicidally, or nematocidally effective amount of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Plutella test

Solvent: 3 parts by weight acetone
Emulsifier: 1 part by weight alkylaryl polyglycol ether To produce a suitable preparation of active compound, 1 part by weight of the active compound is mixed with the stated amount of solvent containing the stated amount of emulsifier and the concentrate is diluted with water to the desired concentration.

Cabbage leaves (*Brassica oleracea*) are sprayed with the preparation of the active compound until dew moist and are then infested with caterpillars of the diamond-back moth (*Plutella maculipennis*).

After the specified periods of time, the degree of destruction is determined as a percentage: 100% means that all the caterpillars are killed whereas 0% means that none of the caterpillars are killed.

The active compounds, the concentrations of the active compounds, the evaluation times and the results can be seen from Table 1.

Emulsifier: 1 part by weight alkylarylpolyglycol ether

To produce a suitable preparation of active compound, 1 part weight of the active compound is mixed with the stated amount of solvent containing the stated amount of emulsifier and the concentrate is diluted with water to the desired concentration.

Cabbage plants (*Brassica oleracea*) which have been heavily infested with peach aphids (*Myzus persicae*) are sprayed with the preparation of the active compound until dripping wet.

After the specified periods of time, the degree of destruction is determined as a percentage: 100% means Table 1

| | Active compound (constitution) | (*Plutella* test) Concentration of active compound in % | Degree of destruction in % after 3 days |
|---|---|---|---|
| (B) | (C$_2$H$_5$O)$_2$P(S)-O-[pyrazole-CH$_3$, NH] (known) | 0.1<br>0.01 | 100<br>0 |
| (A) | (CH$_3$O)$_2$P(S)-O-[pyrazole-CH$_3$, NH] (known) | 0.1 | 0 |
| (2) | (CH$_3$O)$_2$P(S)-O-[pyrazole-NC, SC$_2$H$_5$, CH$_3$] | 0.1<br>0.01 | 100<br>100 |
| (1) | (C$_2$H$_5$O)$_2$P(S)-O-[pyrazole-NC, SC$_2$H$_5$, CH$_3$] | 0.1<br>0.01 | 100<br>100 |
| (3) | (C$_2$H$_5$)(C$_2$H$_5$O)P(S)-O-[pyrazole-NC, SC$_2$H$_5$, CH$_3$] | 0.1<br>0.01 | 100<br>100 |
| (4) | (C$_2$H$_5$O)$_2$P(O)-O-[pyrazole-NC, SC$_2$H$_5$, CH$_3$] | 0.1<br>0.01 | 100<br>100 |

EXAMPLE 2

Myzus test (contact action)

Solvent: 3 parts by weight acetone that all the aphids are killed whereas 0% means that none of the aphids are killed.

The active compounds, the concentrations of the active compounds, the evaluation times and the results can be seen from the following Table 2:

Table 2

| | Active compound (constitution) | (*Myzus* test) Concentration of active compound in % | Degree of destruction in % after 1 day |
|---|---|---|---|
| (B) | (C$_2$H$_5$O)$_2$P(S)-O-[pyrazole-CH$_3$, NH] (known) | 0.1<br>0.01 | 100<br>30 |

Table 2-continued

| | Active compound (constitution) | (Myzus test) Concentration of active compound in % | Degree of destruction in % after 1 day |
|---|---|---|---|
| (A) | 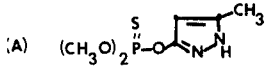 (known) | 0.1 | 0 |
| (2) | 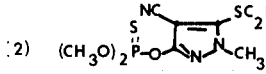 | 0.1<br>0.01<br>0.001 | 100<br>100<br>99 |
| (1) | 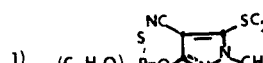 | 0.1<br>0.01<br>0.001 | 100<br>100<br>100 |
| (3) | 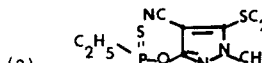 | 0.1<br>0.01<br>0.001 | 100<br>100<br>100 |
| (4) | 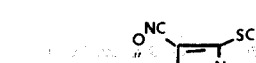 | 0.1<br>0.01<br>0.001 | 100<br>100<br>95 |

EXAMPLE 3

Tetranychus test

Solvent: 3 parts by weight acetone
Emulsifier: 1 part by weight alkylaryl polyglycol ether To produce a suitable preparation of active compound, 1 part by weight of the active compound is mixed with the stated amount of solvent containing the stated amount of emulsifier and the concentrate so obtained is diluted with water to the desired concentration.

Bean plants (*Phaseolus vulgaris*), which have a height of approximately 10–30 cm., are sprayed with the preparation of the active compound until dripping wet. These bean plants are heavily infested with spider mites (*Tetranychus urticae*) in all stages of development.

After the specified periods of time, the effectiveness of the preparation of active compound is determined by counting the dead mites. The degree of destruction thus obtained is expressed as a percentage: 100% means that all the spider mites are killed whereas 0% means that none of the spider mites are killed.

The active compounds, the concentrations of the active compounds, the evaluation times and the results can be seen from Table 3:

Table 3

| | Active compound (constitution) | (*Tetranychus* test) Concentration of active compound in % | Degree of destruction in % after 2 days |
|---|---|---|---|
| (B) | 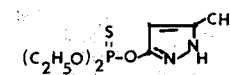 (known) | 0.1 | 0 |
| (A) | 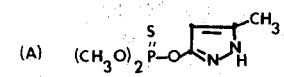 (known) | 0.1 | 0 |

Table 3-continued (Tetranychus test)

| Active compound (constitution) | Concentration of active compound in % | Degree of destruction in % after 2 days |
|---|---|---|
| (2) $(CH_3O)_2\overset{S}{P}-O\underset{N-CH_3}{\overset{NC\diagup\diagdown SC_2H_5}{\diagdown\diagup}}$ | 0.1<br>0.01 | 100<br>100 |
| (1) $(C_2H_5O)_2\overset{S}{P}-O\underset{N-CH_3}{\overset{NC\diagup\diagdown SC_2H_5}{\diagdown\diagup}}$ | 0.1<br>0.01 | 100<br>100 |
| (3) $\underset{C_2H_5O}{C_2H_5\diagdown}\overset{S}{P}-O\underset{N-CH_3}{\overset{NC\diagup\diagdown SC_2H_5}{\diagdown\diagup}}$ | 0.1<br>0.01 | 100<br>100 |
| (4) $(C_2H_5O)_2\overset{O}{P}-O\underset{N-CH_3}{\overset{NC\diagup\diagdown SC_2H_5}{\diagdown\diagup}}$ | 0.1<br>0.01 | 100<br>70 |

EXAMPLE 4

Critical concentration test/soil insects

Test insect: cabbage root fly maggots (*Phorbia brassicae*)

Solvent: 3 parts by weight acetone

Emulsifier: 1 part by weight alkylarylpolyglycol ether

To produce a suitable preparation of active compound, 1 part by weight of active compound is mixed with the stated amount of solvent, the stated amount of emulsifier is added and the concentrate is diluted with water to the desired concentration. The preparation of active compound is intimately mixed with soil. The concentration of the active compound in the preparation is of practically no importance; only the amount of active compound per unit volume of soil, which is given in p.p.m. (for example mg/1), is decisive. The soil is filled into pots and the pots are left to stand at room temperature. After 24 hours, the test animals are put into the treated soil and, after a further 48 hours, the degree of effectiveness of the active compound is determined as a percentage by counting the dead and living test insects. The degree of destruction is 100% when all the test insects have been killed; it is 0% when exactly as many test insects are still alive as in the case of the control.

The active compounds, the amounts applied and the results can be seen from the following Table 4:

Table 4

Soil insecticides (*Phorbia brassicae*-maggots)

| Active compound (constitution) | Degree of destruction in % with a concentration of active compound in ppm of | | | |
|---|---|---|---|---|
|  | 20 | 10 | 5 | 2.5 |
| (1) $\underset{C_2H_5O}{C_2H_5O\diagdown}\overset{S}{P}-O\underset{N-N-CH_3}{\overset{NC\diagup\diagdown SC_2H_5}{\diagdown\diagup}}$ |  | 100 | 100 | 75 |
| (3) $\underset{C_2H_5O}{O_2H_5\diagdown}\overset{S}{P}-O\underset{N-N-CH_3}{\overset{NC\diagup\diagdown S-C_2H_5}{\diagdown\diagup}}$ | 100 | 100 | 95 | 50 |
| (C) $\underset{C_2H_5O}{C_2H_5O\diagdown}\overset{S}{P}-N\underset{\underset{O}{C-CH_2}}{\overset{N=C-CH_3}{\diagup}}$ (known) |  | 0 |  |  |

The following further examples are set forth to illustrate, without limitation, the process for producing the active compounds according to the present invention.

EXAMPLE 5

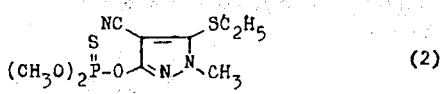 (2)

To 55 g (0.3 mole) of 1-methyl-3-hydroxy-4-cyano-5-ethylmercapto-pyrazole and 45 g of potassium carbonate in 300 ml of acetonitrile there are added 48 g (0.3 mole) of O,O-dimethyl thionophosphoric acid ester chloride, the temperature of the mixture being kept at 35° to 40°C. The reaction mixture is subsequently stirred for 3 hours, poured into water, taken up in benzene, the benzene phase is washed until neutral, dried, and, after the solvent has been drawn off, the residue is slightly distilled. There remain behind 67 g (73% of theory) of the desired O,O-dimethyl-O-[1-methyl-4-cyano-5-ethylmercapto-pyrazol(3)yl]-thionophosphoric acid ester.

For $C_9H_{14}N_3O_3PS$ (molecular weight 307)

|  | N | S | P |
|---|---|---|---|
| Calculated: | 13.7%; | 20.85%; | 10.1%; |
| Found: | 13.9%; | 20.30%; | 9.7%. |

EXAMPLE 6

By a procedure analogous to Example 5, the following compounds are prepared:

| | Formula | Refractive index | Yield (% of theory) |
|---|---|---|---|
| (1) | (C$_2$H$_5$O)$_2$P(S)-O-[NC, SC$_2$H$_5$, N-CH$_3$ pyrazole] | $n_D^{26} = 1.5239$ | 87 |
| (3) | (C$_2$H$_5$)(C$_2$H$_5$O)P(S)-O-[NC, SC$_2$H$_5$, N-CH$_3$ pyrazole] | $n_D^{25} = 1.5352$ | 67 |
| (4) | (C$_2$H$_5$O)$_2$P(O)-O-[NC, SC$_2$H$_5$, N-CH$_3$ pyrazole] | $n_D^{25} = 1.5042$ | 85 |
| (5) | (C$_2$H$_5$O)$_2$P(O)-O-[NC, SC$_3$H$_7^i$, N-CH$_3$ pyrazole] | $n_D^{23} = 1.5194$ | 80 |
| (6) | (CH$_3$O)$_2$P(S)-O-[NC, SC$_3$H$_7^i$, N-CH$_3$ pyrazole] | $n_D^{23} = 1.5376$ | 79 |
| (7) | (CH$_3$)(iC$_3$H$_7$O)P(S)-O-[NC, SC$_3$H$_7^i$, N-CH$_3$ pyrazole] | 1.5321 | 86 |

The 1-methyl-3-hydroxy-4-cyano-5-ethylmercaptopyrazole required as starting material can be obtained for example as follows:

EXAMPLE 7

115 g (0.5 mole) of the compound of the following formula

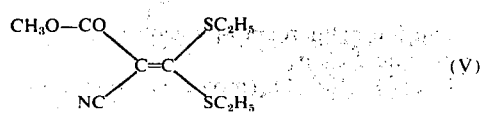

(V)

(prepared according to "Chemische Berichte", Vol. 95, (1962) 2861 and 2870) by reacting methyl cyanoacetate with carbon disulfide in the presence of an alkali, followed by reaction with two moles of ethyl halide are heated together with 23 g of methylhydrazine in 500 ml of absolute ethanol for one hour at 70° to 75°C. Ethyl sulfide is distilled off and the reaction solution is cooled. The mixture is then diluted with 500 ml of water and the reaction product is allowed to crystallize out. The crystals are filtered off with suction, washed with ether and dried on clay. There remain behind 50 g (55% of theory) of the desired substance of melting point 192°C.

It will be appreciated that the instant specification and examples are set forth by way of illustration and not limitation, and that various modifications and changes may be made without departing from the spirit and scope of the present invention.

What is claimed is:

1. A method of combating insects or acarids which comprises applying to said insects, acarids or a habitat thereof an insecticidally or acaricidally effective amount of a compound of the formula

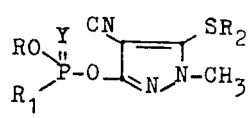

in which
R is alkyl of 1–6 carbon atoms,
$R_1$ is alkyl or alkoxy of 1–6 carbon atoms,
$R_2$ is alkyl of 2–4 carbon atoms, and
Y is oxygen or sulfur.

2. The method according to claim 1 in which R and $R_1$ each is of 1–4 carbon atoms and $R_2$ is of 2 or 3 carbon atoms.

3. The method according to claim 1, wherein said compound is 0,0-dimethyl-0-[1-methyl-4-cyano-5-ethylmercaptopyrazol(3)yl]-thionophosphoric acid ester of the formula

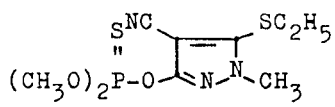

4. The method according to claim 1, wherein said compound is 0,0-diethyl-0-[1-methyl-4-cyano-5-ethyl mercapto-pyrazol(3)yl]-thionophosphoric acid ester of the formula

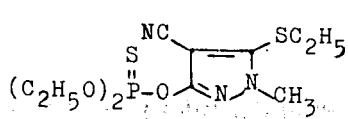

5. The method according to claim 1, wherein said compound is 0-ethyl-0-[1-methyl-4-cyano-5-ethyl-mercapto-pyrazol(3)yl]-ethanethionophosphonic acid ester of the formula

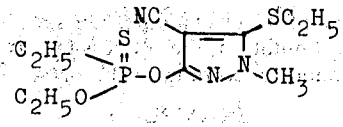

6. The method according to claim 1, wherein said compound is 0,0-diethyl-0-[1-methyl-4-cyano-5-ethyl-mercapto-pyrazol(3)yl]-phosphoric acid ester of the formula

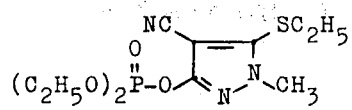

7. The method according to claim 1, wherein said compound is 0,0-diethyl-0-[1-methyl-4-cyano-5-isopropyl-mercapto-pyrazol(3)yl]-phosphoric acid ester of the formula

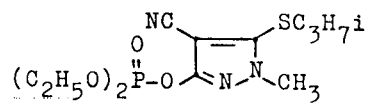

8. The method according to claim 1, wherein said compound is 0,0-dimethyl-0-[1-methyl-4-cyano-5-isopropyl-mercapto-pyrazol(3)yl]-thionophosphoric acid ester of the formula

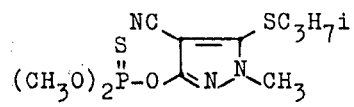

9. The method according to claim 1, wherein said compound is 0-iospropyl-0-[1-methyl-4-cyano-5-isopropylmercapto-pyrazol(3)yl]-methanethionophosphonic acid ester of the formula

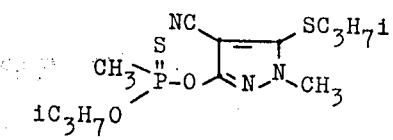

10. An insecticidal or acaricidal composition comprising an insecticidally or acaricidally effective amount of a compound of the formula

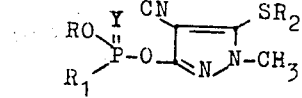

in which
R is alkyl of 1–6 carbon atoms,
$R_1$ is alkyl or alkoxy of 1–6 carbon atoms,
$R_2$ is alkyl of 2–4 carbon atoms, and
Y is oxygen or sulfur,
in admixture with a diluent.

11. The composition according to claim 10, in which said compound is
0,0-dimethyl-0-[1-methyl-4-cyano-5-ethylmercaptopyrazol(3)yl]-thionophosphoric acid ester,
0,0-diethyl-0-[1-methyl-4-cyano-5-ethylmercaptopyrazol(3)yl]-thionophosphoric acid ester, 0-ethyl-0-[1-methyl-4-cyano-5-ethylmercapto-pyrazol(3)yl]-ethanethionophosphonic acid ester,
0,0-diethyl-0-[1-methyl-4-cyano-5-ethylmercapto-pyrazol(3)yl]-phosphoric acid ester,
0,0-diethyl-0-[1-methyl-4-cyano-5-isopropylmercapto-pyrazol(3)yl]-phosphoric acid ester,
0,0-dimethyl-0-[1-methyl-4-cyano-5-isopropylmercapto-pyrazol(3)yl]-thionophosphoric acid ester, or
0-isopropyl-0-[1-methyl-4-cyano-5-isopropylmercapto-pyrazol(3)yl]-methanethionophosphonic acid ester.

* * * * *